United States Patent
Secrist, III et al.

(10) Patent No.: US 6,576,621 B1
(45) Date of Patent: Jun. 10, 2003

(54) PREPARATION OF THIOARABINOFURANOSYL COMPOUNDS AND USE THEREOF

(75) Inventors: John A. Secrist, III, Birmingham, AL (US); Kamal N. Tiwari, Birmingham, AL (US); John A. Montgomery, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 09/493,247

(22) Filed: Jan. 28, 2000

Related U.S. Application Data

(63) Continuation of application No. PCT/US99/16630, filed on Jul. 23, 1999.
(60) Provisional application No. 60/093,869, filed on Jul. 23, 1998.

(51) Int. Cl.$^7$ .............................. A61K 9/00; A61K 7/16
(52) U.S. Cl. ............................................ 514/49; 514/43
(58) Field of Search ...................... 514/43, 49

(56) References Cited

FOREIGN PATENT DOCUMENTS

| | | | |
|---|---|---|---|
| JP | 9-25289 | 1/1997 | |
| JP | 9-249690 | 9/1997 | |
| WO | WO 91/04033 | 4/1991 | |
| WO | WO 91/04982 | 4/1991 | |
| WO | WO 99/43690 A1 | 9/1999 | |
| WO | WO 9943690 | * 9/1999 | .................. 514/49 |

OTHER PUBLICATIONS

Ototani et al., J. Med. Chem. (1974), 17(5), 535–7 Abstract Only.*
XP–002174620, Chemical Abstracts 118 (5), Feb. 1, 1993, Abstract No. 32613 and Med. Chem. Res. 2 (3), 1992:154–164.
XP–000651717, Journal of Medicinal Chemistry 17 (5), May 1, 1974:535–537.
Reitz et al, J. Med. Chem. 1994, 37, 3561–3578.
Reist et al, The Journal of Organic Chemistry, vol. 33, No. 1, Jan. 1968, 189–192.
Satoh et al, Bioorganic & Medicinal Chemistry Letters 8 (1998), 989–992.
Secrist, III et al, Nucleosides & Nucleotides, 14(3–5), 675–686 (1995).
Whistler et al, The Journal of Organic Chemistry, Feb. 1970, Notes 519–Notes 521.
Whistler et al, J. Org. Chem., vol. 36, No. 1, 1971, 108–110.
Yoshimura et al, J. Org. Chem. 1997, 62, 3140–3152.
Yoshimura et al, Nucleic Acids Symposium Series No. 35, 15–16, 1996.
Yoshimura et al, J. Med. Chem. 1997, 40, 2177–2183.
Yoshimura et al, Nucleic Acids Symposium Series No. 34, 1995, 21–22.
Ototani et al, J. Med. Chem., 17(5), 1974, 535–537—Abstract.
Lin et al, J. Med. Chem. 1985, 28, 1194–1198.
Machida et al, 10$^{th}$ International Conference on Antiviral Research, Poster #120, Apr. 10, 1997.
Michael et al, J. Med. Chem. 1993, 36, 3431–3436.
Nagahara et al, J. Med. Chem. 1990, 33, 407–415.

* cited by examiner

*Primary Examiner*—Jerome D. Goldberg
(74) *Attorney, Agent, or Firm*—Connolly Bove Lodge & Hutz LLP

(57) ABSTRACT

Patients suffering from cancer are treated by being administered a compound represented by the following formula:

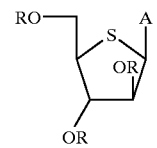

wherein
each R individually is H or an aliphatic or aromatic acyl group;
A is selected from the group consisting of

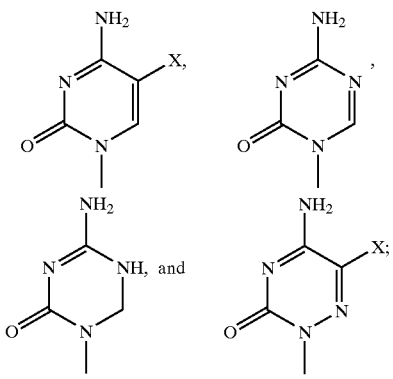

wherein X is selected from the group consisting of hydrogen, fluorine, alkoxy, alkyl, haloalkyl, alkenyl, haloalkenyl, alkynyl, amino, monoalkylamino, dialkylamino, cyano and nitro. The above compounds also inhibit DNA replication in mammalian cells,

21 Claims, 2 Drawing Sheets

PREPARATION OF THIOARABINOFURANOSYL COMPOUNDS AND USE THEREOF

This application is a continuation application of PCT/US99/16630, filed Jul. 23, 1999 which designated the U.S. and which claims priority from U.S. Provisional Patent Application Ser. No. 60/093,869 filed Jul. 23, 1998.

FEDERALLY SPONSORED RESEARCH AND DEVELOPMENT

This invention was supported by Grant CA-34200 from National Institutes of Health.

TECHNICAL FIELD

The present invention is concerned with treating patients suffering from cancer by administering to the patients certain thioarabinofuranosyl compounds. Compounds employed according to the present invention have exhibited good anticancer activity. Compounds employed according to the present invention are in the beta configuration as contrasted to the alpha configuration, which failed to exhibit anticancer activity. The present invention also relates to inhibiting DNA replication in a mammalian cell by contacting with the thioarabinofuranosyl compounds. The present invention also relates to a new process for preparing the compounds employed according to the present invention.

BACKGROUND OF INVENTION

Vast amounts of research have accrued over the years related to developing treatments against cancers to inhibit and kill tumor cells. Some of this research has resulted in achieving some success in finding clinically approved treatments. Nevertheless, efforts continue at an ever-increasing rate in view of the extreme difficulty in uncovering promising anticancer treatments. For example, even when a compound is found to have cytotoxic activity, there is no predictability of it being selective against cancer cells.

One particular compound that has been used rather widespread is cytosine arabinoside, commonly referred to as Ara-C.

SUMMARY OF INVENTION

It has been found according to the present invention that certain thioarabinofuranosyl cytosine compounds are suitable as anticancer agents. The presence of the thio sugar moiety surprisingly makes it possible to achieve good anti-tumor activity. More particularly, the present invention relates to treating a mammalian host in need of an anticancer treatment by administering to the host an effective anticancer amount of at least one compound represented by the following formula 1:

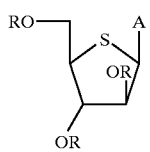

wherein
each R individually is H or an aliphatic or aromatic acyl group;

A is selected from the group consisting of

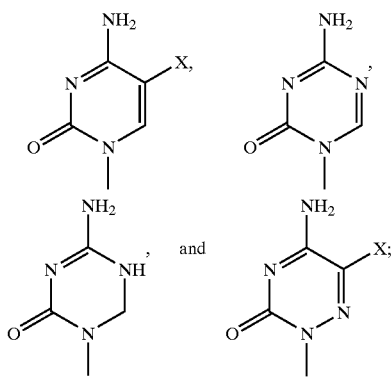

X is selected from the group consisting of hydrogen, fluoro, alkoxy, alkyl, haloalkyl, alkenyl, haloalkenyl, alkynyl, amino, monoalkylamino, dialkylamino, cyano and nitro.

It has also been found according to the present invention that the above-disclosed compounds of formula 1 can be used to inhibit DNA replication in a mammalian cell by contacting the cell with at least one of these compounds.

The present invention is also concerned with a process for preparing the above-identified compounds. The compounds employed according to the present invention can be prepared by:

A) reacting a 2,3,5-tri-O-aryl or alkyl-4-xylose diaryl or dialkyl dithioacetal such as 2,3,5-tri-O-benzyl-L-xylose-dibenzyl dithioacetal in the presence of a leaving group at the 4 hydroxyl to produce the corresponding 1,4-dithio-D-arabinofuranoside such as benzyl 2,3,5-tri-O-benzyl-1,4-dithio-D-arabinofuranoside;

B) subjecting the product from step A) to acidolysis to form the corresponding O-acetyl-4-thio-D arabinofuranose such as 2,3,5-tri-O-benzyl-1-O-acetyl-4-thio-D-arabinofuranose;

C) reacting the product of step B with a cytosine, a 5- or 6-aza compound or a suitably blocked derivative thereof forming a corresponding 4-thio-α,β-D-arabinofuranosyl) compound such as, in the case of cytosine, 1-(2,3,5-tri-O-benzyl-4-thio-α,β-D-arabinofuranosyl cytosine;

D) converting the compound of step C) by hydrolysis to the corresponding thio sugar derivative such as 1-(4-thio-α,β-D-arabinofuranosyl) cytosine;

E) separating out the α form of the anomeric mixture of step D) to thereby obtain the desired compound of formula 1, such as 1-(4-thio-β-D-arabinofuranosyl) cytosine.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description contained herein is to be regarded as illustrative in nature and not as restrictive.

BEST AND VARIOUS MODES FOR CARRYING OUT INVENTION

Figure 1B:
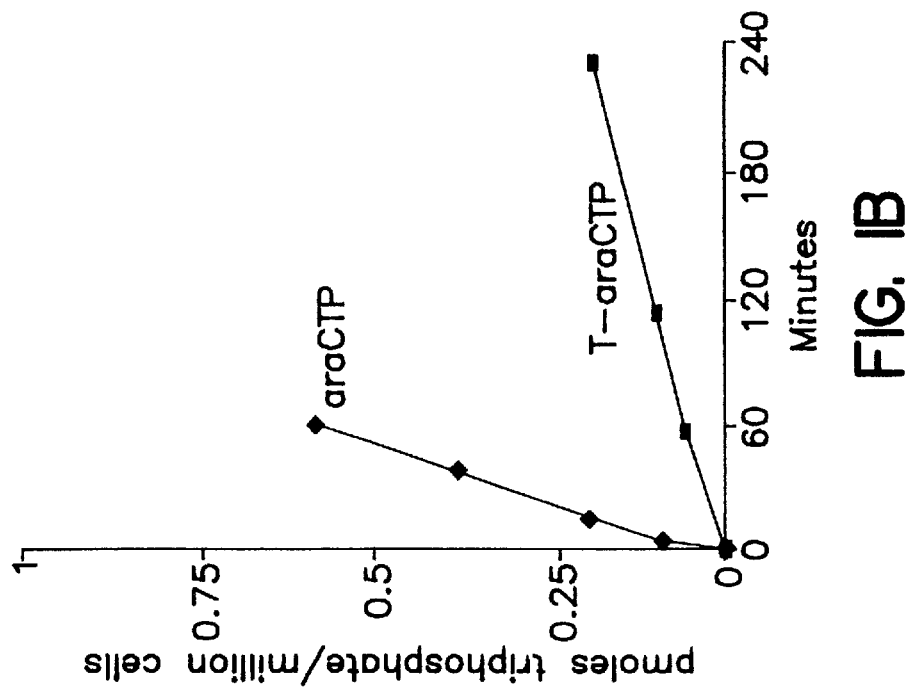
FIGS. 1a and 1b are graphs showing metabolism of 2-deoxycytidine, 2'-deoxythiocytidine, ara c and thio ara-c to their respective triphosphates.

The present invention is related to treating a mammalian host in need of an anticancer treatment, which comprises administering to the host an effective anticancer amount of at least compound represented by the formula 1:

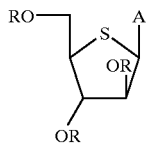

Each R in formula 1 individually is preferably H or an aliphatic or aromatic acyl group. Typical aliphatic acyl groups contain from 1 to 6 carbon atoms and include formyl, acetyl, and propionyl. Typical aromatic acyl groups include unsubstituted and alkyl substituted aromatic groups containing 7–10 carbon atoms in the aromatic group. When substituted, the alkyl group typically contains 1–6 carbon atoms. Typical aromatic acyl groups include benzoyl and para-toloyl.

A in formula 1 is preferably

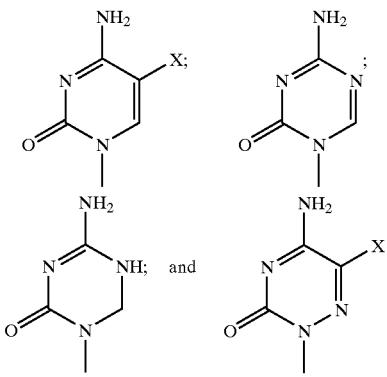

Suitable monoalkylamino groups for X contain 1–6 carbon atoms and include monomethylamino, monoethylamino, mono-isopropylamino, mono-n-propylamino, mono-isobutyl-amino, mono-n-butylamino and mono-n-hexylamino. The alkyl moiety can be straight or branched chain.

Suitable dialkylamino groups for Y and X contain 1–6 carbon atoms in each alkyl group. The alkyl groups can be the same or different and can be straight or branched chain. Examples of some suitable groups are dimethylamino, diethylamino, ethylmethylamino, dipropylamino, dibutylamino, dipentylamino, dihexylamino, methylpentylamino, ethylpropylamino and ethylhexylamino.

Suitable halogen groups for X include Cl, Br and F.

Suitable alkyl groups for X typically contain 1–6 carbon atoms and can be straight or branched chain. Some examples are methyl, ethyl, i-propyl, n-propyl, i-butyl, n-butyl, pentyl and hexyl.

Suitable haloalkyl groups typically contain 1–6 carbon atoms and can be straight or branched chain and include Cl, Br or F substituted alkyl groups including the above specifically disclosed alkyl groups.

Suitable alkoxy groups typically contain 1–6 carbon atoms and include methoxy, ethoxy, propoxy and butoxy.

Suitable alkenyl groups typically contain 2–6 carbon atoms and include ethenyl and propenyl.

Suitable haloalkenyl groups typically contain 1–6 carbon atoms and include Cl, Br or F substituted alkenyl groups including the above specifically disclosed alkenyl groups.

Suitable alkynyl groups typically contain 1–6 carbon atoms and include ethynyl and propynyl.

The preferred compound employed according to the process of the present invention is 1-(4-thio-β-D-arabinofuranosyl) cytosine.

The present invention is suitable for treating mammalian hosts including humans suffering from cancer including melanoma, prostate cancer, mammary cancer, renal cancer, colon cancer, lung cancer, leukemias and lymphomas.

The compounds employed according to the present invention can be prepared by reacting a 2,3,5-tri-O-aryl or alkyl-4-xylose diaryl or dialkyl dithioacetal such as 2,3,5-tri-O-benzyl-L-xylose-dibenzyl dithioacetal in the presence of a bearing group at the 4 hydroxyl position to produce the corresponding 1,4-dithio-D-arabinofuranoside such as benzyl 2,3,5-tri-O-benzyl-1,4-dithio-D-arabinofuranoside. This step can be carried out using phosphine, iodine and imidazole. The product from the above step is subjected to acidolysis to form the corresponding O-acetyl-4-thio-D ara-binofuranose such as 2,3,5-tri-O-benzyl-1-O-acetyl-4-thio-D-arabinofuranose. For instance, acetic acid in the presence of mercuric acetate can be employed.

The product of the above step is reacted with a cytosine, a 5- or 6-aza compound or a suitably blocked derivative thereof forming a corresponding 4-thio-α,β-D-arabinofuranosyl compound such as, in the case of cytosine, 1-(2,3,5-tri-O-benzyl-4-thio-α,β-D-arabinofuranosyl) cytosine. Suitable blocked derivatives include acyl and trimethylsilylated derivatives. The compound of the above step is converted by hydrolysis to the corresponding thio sugar derivative such as 1-(4-thio-α,β-D-arabinofuranosyl) cytosine.

The α form of the anomeric mixture of the above step is separated out to thereby obtain the desired compound of formula 1, such as 1-(4-thio-β-D-arabinofuranosyl) cytosine.

Compounds according to the present invention can be prepared by the process sequence shown in scheme 1 and examples 1 and 2 described hereinbelow, wherein the preferred compound, 1-(4-thio-β-D-arabinofuranosyl) cytosine is illustrated for purposes of facilitating an understanding of the process sequence. The precursor employed, 2,3,5-thio-O-benzyl-L-xylose dibenzyl dithioacetal, can be produced by the process described by Secrist, III et al, "The Synthesis and Biological Activity of Certain 4'-Thionucleosides, Nucleosides & Nucleotides, 14 (3–5), 675–686 (1995), disclosure of which is incorporated herein by reference. The process of the present invention provides for a relatively efficacious method for producing significant quantities of the desired compound. Prior art techniques are extremely complicated and not readily suitable for producing desired amounts of the compounds.

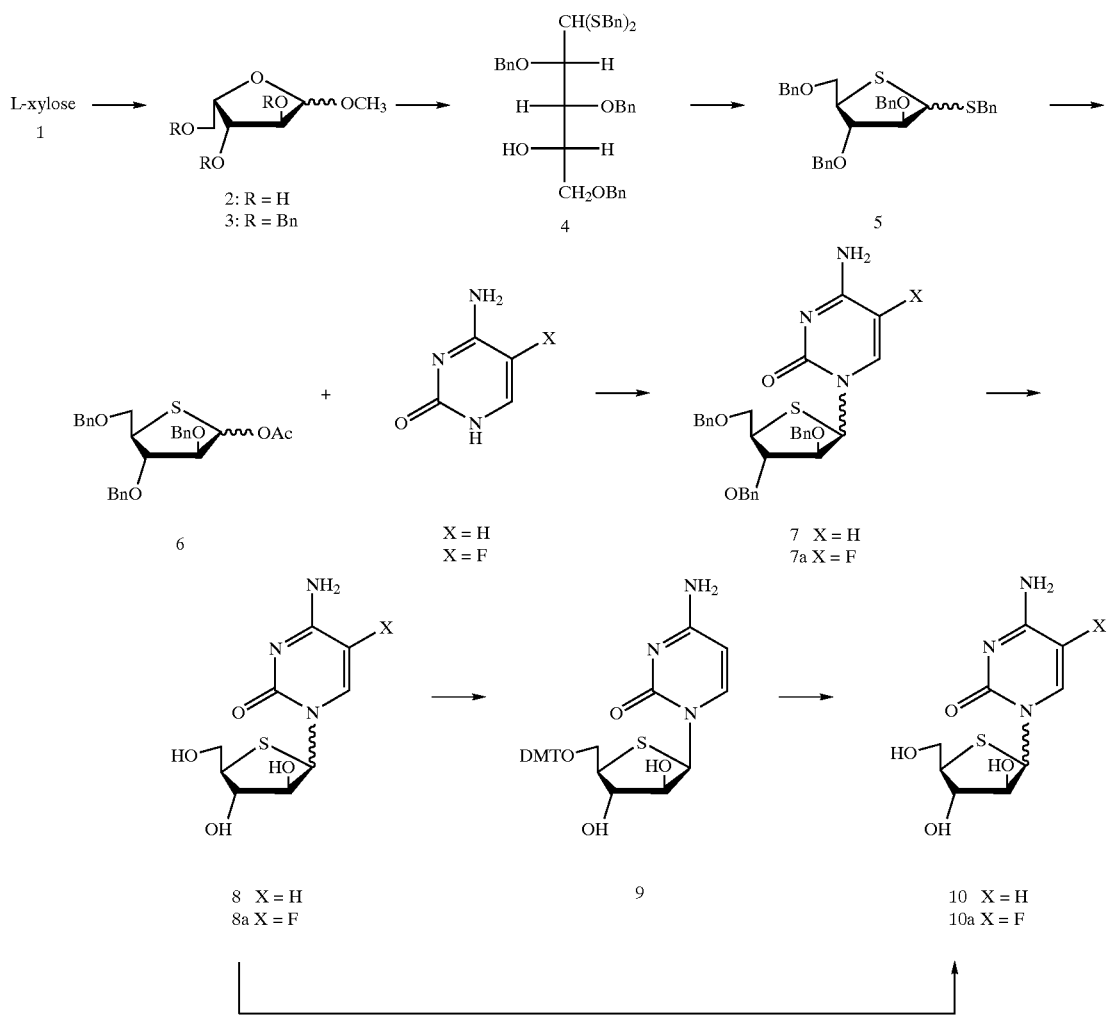

The pharmaceutically acceptable effective dosage of the active compound of the present invention to be administered is dependent on the species of the warm-blooded animal (mammal), the body weight, age and individual condition, and on the form of administration.

The pharmaceutical composition may be oral, parenteral, suppository or other form which delivers the compounds used in the present invention into the bloodstream of a mammal to be treated.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) typically contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mu of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The following non-limiting examples are presented to further illustrate the present invention.

EXAMPLE 1

Preparation of 1-(4-Thio-β-D-Arabinofuranosyl) Cytosine 2,3,5-Tri-O-benzyl-L-xylose Dibenzyl Dithioacetal (4). L-Xylose (1, 25 g, 167 mmol) was stirred for 5 hours in 0.5% hydrogen chloride in methanol (675 mL) at room temperature and then neutralized with Amberlite IRA-400 OH anion exchange resin. The filtrate and washings were combined and evaporated to dryness and the crude product was purified by silica gel chromatography ($CHCl_3$/MeOH, 92:8) to afford 26.2 g of methyl L-xylofuranoside (2, 95% yield) as an α and β (1:1) mixture. MS 164 $(M)^+$, 165 $(M+H)^+$, 133 $(M-OCH_3)^+$.

To an ice-cold solution of 2 (10 g, 60.9 mmol) in dry tetrahydrofuran (350 mL) was added sodium hydride (60% dispersion in mineral oil, 14.8 g, 370 mmol) and the reaction mixture was stirred for 15 min under $N_2$. To this reaction mixture was added solid tetrabutylammonium iodide (0.36 g, 0.96 mmol) followed by a dropwise addition of benzyl bromide (36.6 g, 214 mmol). The reaction mixture was stirred for 3 days at room temperature. After the addition of methanol (25 mL) the solution was evaporated under reduced pressure, and the crude product was purified by silica gel chromatography (cyclohexane/EtOAc, 9:1) to afford pure methyl 2,3,5-tri-O-benzyl-L-xylofuranoside (3, 23 g, 87% yield). MS 435 $(M+H)^+$, 433 $(M-H)^+$, 403 $(M-OCH_3)^+$; $^1H$ NMR ($CDCl_3$) δ 7.38–7.25 (m, 30H, aromatic H=s), 4.94 (d, 1H, H-1α, $J_{1,2}$=4.3 Hz), 4.87 (d, 1H, H-1β, $J_{1,2}$=0.9 Hz), 4.64–4.45 (m, 12H, $PhCH_2$'s), 4.37 (m, 1H, H-4α), 4.27 (dt, 1H, H-4β, $J_{4,5a}$=3.7 Hz, $J_{4,5b}$=6.5 Hz, $J_{3,4}$=6.2 Hz), 4.17 (t, 1H, H-3α, $J_{3,4}$=6.9 Hz, $J_{2,3}$=5.6 Hz), 4.07 (dd, 1H, H-3β, $J_{3,4}$=6.2 Hz, $J_{2,3}$=2.5 Hz), 4.00 (dd, 1H, H-2α, $J_{2,3}$=5.6 Hz), 3.95 (t, 1H, H-2β, $J_{2,3}$=2.5 Hz), 3.70 (dd, 1H, H-5aα, $J_{4,5a}$=4.5 Hz, $J_{5a,5b}$=10.4 Hz), 3.66 (dd, 1H, H-5aβ, $J_{4,5a}$=3.7 Hz, $J_{5a,5b}$=10.7 Hz), 3.54 (dd, 1H, H-5bα, $J_{4,5b}$=7.5 Hz), 3.49 (dd, 1H, H-5bβ, $J_{4,5b}$=6.5 Hz).

To a solution of 3 (42 g, 97 mmol) in dichloromethane (1000 mL) were added benzyl mercaptan (49.6 g, 400 mmol) and stannic chloride (4.93 g, 18.9 mmol), and the reaction mixture was stirred at room temperature overnight. After neutralization with 5% aqueous $NaHCO_3$ (750 mL), the organic layer was separated and the aqueous layer was extracted with dichloromethane (500 mL). The combined organic layers were evaporated, and crude 4 was purified by silica gel chromatography (cyclohexane/EtOAc, 99:1) to afford 4 (8.53 g, 57%) of sufficient purity to carry forward. MS 657 $(M+Li)^+$; $^1H$ NMR ($CDCl_3$) δ 7.35–7.29 (m, 19H, aromatic H=s), 7.19–7.13 (m, 4H, aromatic H=s), 7.01–6.96 (m, 2H aromatic H=s), 4.86 (d, 1H, PhCHH, J=11.1 Hz), 4.70 (two overlapping d=s, 2H, PhCHH, PhCHH, J=11.1 Hz, J=11.2 Hz), 4.43 (d, 1H, PhCHH, 11.2 Hz), 4.40 (d, IH, PhCHH, J=11.9 Hz), 4.36 (d, 1H, PhCHH, J=11.9 Hz), 4.07 (dd, 1H, H-2, $J_{1,2}$=3.0 Hz, $J_{2,3}$=7.5 Hz), 3.75–3.67 (m, 4H, two $PhCH_2$=s), 3.68 (d, 1H, H-1, $J_{1,2}$=3.0 Hz), 3.36–3.25 (m, 2H, H-4, H-5a), 3.15–3.12 (m, 1H, H-5b), 2.22 (d, 1H, 4-OH, J=6.2 Hz).

2,3,5-Tri-O-benzyl-1-O-acetyl-4-thio-D-arabinofuranose (6). To a solution of 4 (13.0 g., 20 mmol) in dry 2:1 toluene/acetonitrile (200 mL) were added triphenylphosphine (15.7 g, 60 mmol), iodine (12.7 g, 50 mmol) and imidazole (5.44 g, 80 mmol). The reaction mixture was stirred at 90 1 C. for 24 h after which time the solution was evaporated to dryness. The crude product was purified by silica gel chromatography (cyclohexane/EtOAc, 4:1) to afford benzyl 2,3,5-tri-O-benzyl-1,4-dithio-D-arabinofuranoside as a syrup (5, 9.0 g, 83%). MS 543 $(M+H)^+$; $^1H$ NMR ($CDCl_3$) δ 7.40–7.20 (m, 20H, aromatic H=s), 4.69–4.42 (m, 6H, three $PhCH_2O$=s), 4.37 (m, 1H, H-1), 4.20 (m, 2H, H-2, H-3), 3.87 (s, 2H, $PhCH_2S$—), 3.80 (dd, 1H, H-5a, $J_{4,5a}$=7.4 Hz, $J_{5a,5b}$=9.3 Hz), 3.55 (dd, 1H, H-5b, $J_{4,5b}$=7.1 Hz), 3.47 (m, 1H, H-4). Anal. ($C_{33}H_{34}O_3S_2$ @ 0.25 $H_2O$) C, H.

To a suspension of mercuric acetate (7.29 g, 22.9 mmol) in acetic acid (96 g) was added 5 (5.42 g, 10 mmol), and the resulting mixture was stirred at room temperature for 2 h. The reaction mixture was diluted with dichloromethane (200 mL) and washed successively with water, saturated aqueous NaHCO$_3$ and 5% aqueous KCN solution. The organic layer was dried over Na$_2$SO$_4$ and concentrated. Chromatography of the crude product using cyclohexane:ethylacetate (98:2) as eluent gave a mixture of α and β (1:1) anomers of 6 (3.73 g, 78%) as a colorless syrup. MS 479 (M+H)$^+$; $^1$H NMR (CDCl$_3$) δ 7.35–7.23 (m, 15H, aromatic H=s), 6.07 (d, 0.25H, H-1β, J$_{1,2}$=4.0 Hz), 5.98 (d, 0.75H, H-1α, J$_{1,2}$=2.8 Hz), 4.83–4.45 (m, 6H, PhCH$_2$'s), 4.26 (dd, 0.75H, H-2α, J$_{2,3}$=5.4 Hz), 4.17–4.11 (m, 0.5H, H-2β, H-3β), 4.03 (t, 0.75H, H-3α, J$_{3,4}$=6 Hz), 3.80–3.67 (m, 1.25H, H-4α, H-5aα, H-5aβ), 3.53–3.39 (m, 1.75H, H-5bα, H-4β, H-5bβ), 2.06 (s, 3H, CH3-α and CH3-β). Anal. (C$_{28}$H$_{30}$O$_5$S @ 0.75 H$_2$O) C, H.

1-(2,3,5-Tri-O-benzyl-4-thio-α,β-D-arabinofuranosyl) cytosine (7). To a suspension of 1-O-acetyl 2,3,5-tri-O-benzyl-4-thio-D-arabinoftiranose (478 mg, 1 mmol) and cytosine (111.0 mg, 1 mmol) in anhydrosis acetonitrile (25 mmol) were added consecutively hexamethyldisilazane (HMMDS, 162 mg, 1 mmol) and chlorotrimethylsilane (TMSCl, 434 mg, 4 mmol), and the mixture was stirred at room temperature for 0.5 hours. This solution was cooled to −78° C. Trimethylsilyltrifluoromethane sulfonate (267 mg, 1.2 mmol) was added and the resulting solution was stirred at −78° C. for another 2.5 h, after which time the reaction was essentially complete. The mixture was warmed to room temperature, concentrated to a small volume (5 mL), diluted with methylene chloride (50 mL) and then washed with water (20 mL) followed by saturated sodium bicarbonate and water. The organic layer was dried over MgSO$_4$ and evaporated to dryness. The residue was purified by chromatography over silica gel (50 g. elution with CHCl$_3$/MEOH 98:2) to afford 7 (412 mg 77.5%) as a colorless syrup TLC (95:5 CHCl$_3$/MEOH) R$_f$ 0.65; MS z/e 536 (M+Li)$^+$.

$^1$H NMR (CDCl$_3$) δ 8.22 (d, 1, H-6$_β$, J=7.6); (d, 1, H-6$_α$, J$_{5,6}$=7.5 Hz); 7.38–7.09 (m, 30, aromatic H's); 6.65 (d, 1, H-1'$_β$, J$_{1',2'}$=5.7 Hz); 6.36 (d, 1, H-1'$_α$, J$_{1',2'}$=1.2 Hz); 5.44 (d, 1, H-5$_β$); 5.26 (d, 1, H-5$_β$); 4.97–4.33 (overlapping multiplets, 12, C$_6$H$_5$CH$_2$), 4.26 (dd, 1 H-2'$_β$, J$_{2',3'}$=6.8 Hz); 4.22 (m, 1, H-3'$_α$, J$_{3',4'}$=1 Hz); 4.16 (dd, 1, H-3'$_β$, J$_{3',4'}$=6.4 Hz); 4.13 (m, 1, H-2'$_α$, J$_{2',3'}$=1.7 Hz); 3.91 (m, 1, H-4'$_α$); 3.78 (m, 1, H-5'$_α$); 3.73–3.63 (m, 2, H-5'$_β$); 3.55 (m, 1, H-5'$_α$); 3.46 (m, 1, H-4'$_β$).

1-(4-Thio-α,β-D-arabinofuranosyl) cytosine (8). To a solution of boron trichloride (1 M solution) in dry dichloromethane (7 mL, 7mmol) cooled to −78° C., was added dropwise over a period of 30 min, a solution of compound 7 (265 mg, 0.5 mmol) in dry dichloromethane (10 mL). Stirring was continued overnight at −20° C. The solvent was removed in vacuo and the residue was coevaporated with dichloromethane (4×20 mL). The residue was neutralized with saturated NaHCO$_3$ (25 mL) and washed with chloroform (15 mL). The aqueous layer was applied to a cation exchange (H$^+$) column and eluted with water to remove salts and then eluted with 1N NH$_4$OH to obtain the desired compound 8 (110 mg, 85%) MS z/e 260(M+H)$^+$.

$^1$H NMR (Me$_2$SO-d$_6$) δ 7.94 (d, 0.67, H-6-β, J$_{5,6}$=7.5 Hz); 7.90 (d, 0.33, H-6α, J$_{5,6}$=7.5 Hz); 7.17–7.03 (overlapping bs, 2, NH's); 6.33 (d, 0.67, H-1'β, J$_{1',2'}$=4.6 Hz); 5.86 (d, 0.33, H-1'α, J$_{1',2'}$=7.3 Hz); 5.77 (d, 0.33, H-5α); 5.70 (d, 0.67, H-5β); 5.61 and 5.59 (overlapping doublets, 1,2'-OHβ, J$_{2',2'-OH}$=5.1 Hz, 2'-OHα, J$_{2',2'-OH}$=5.9 Hz); 5.47 (d, 0.33, 3'-OHα, J$_{3',3'-OH}$=5.1 Hz); 5.38 (d, 0.67, 3'-OHβ, J 3',3'-OH=4.2 Hz); 5.08 (t, 0.67, 5'-OHβ, J$_{5',5'-OH}$= 5.4 Hz); 4.90 (t, 0.33, 5'-OHα, J$_{5',5'-OH}$=5.2 Hz); 4.00–3.93 (m, 1.67, H-2'$_α$, H-2'$_β$, H-3'$_β$); 3.86–3.76 (m, 1, H-5'$_α$ and H-5'$_β$); 3.67–3.55 (m, 1, H-5'$_β$+H-3'$_α$); 3.49–3.33 (m, 0.67, H-4'$_α$, H-5'$_α$); 3.17 (m, 0.67, H-4'$_β$).

1-(5-O-dimethoxytrityl-4-thio-β-D-arabinofuranosyl) cytosine (9). To a solution of compound 8 (100 mg, 0.38 mmol) in dry pyridine (10 mL) was added 4,4'-Dimethoxytritylchloride (135 mg, 0.6 mmol) and the solution was stirred for 2 at room temperature. The reaction mixture was evaporated to dryness and the crude was dissolved in ethyl acetate (20 mL) and washed with water and evaporated to dryness to afford a solid which was purified on silica gel column (CHCl$_3$/MeOH 98:2) to obtain pure compound 9 (96 mg, 90% based on 1:1 mixture of α, β-mixture of 8). MS z/e 568.3 (M+Li)$^+$.

$^1$H NMR (Me$_2$SO-d$_6$) δ 7.77 (d, 1, H-6, J$_{5,6}$=7.5 Hz); 7.42–7.23 (m, 9, aromatic H's); 7.17 (bs, 1, NH); 7.05 (bs, 1, NH); 6.91–6.88 (m, 4, aromatic H's); 6.36 (d, 1, H-1', J$_{1',2'}$=4.8 Hz); 5.65 (d, 1, H-5); 5.76 (d, 1, 2'-OH, J$_{2',2'-OH}$= 4.6 Hz); 5.43 (d, 1, 3'-OH, J$_{3',3'-OH}$=3.3 Hz); 3.98–3.91 (m, 2, H-2', H-3'); 3.75 (s, 6, OCH$_3$); 3.39–3.25 (m, B, H-4', H-5').

1-(4-Thio-β-D-arabinofuranosyl) cytosine (10). Compound 9 (90 mg, 0.16 mmol) was treated with trifluoroacetic acid (22 mg) in chloroform (5 mL) at room temperature for 10 min. The reaction mixture was neutralized with aq. NaHCO$_3$ and the aqueous layer was applied on a cation exchange column which was eluted first with water to remove salt and finally with 1N NH$_4$OH to afford compound 10 (35 mg, 85%), mp218–220° C. (lit[1] 221–222° C.); MS z/e 260(M+H)$^+$.

[1] Ototani, H.; Whistler, R. L. Preparation and Antitumor Activity of 4'-Thio Analogs of 2,2'-Anhydro-1-β-D-arabinofuranosylcytosine. *J. Med. Chem.* 1974, 17, 535–537.

$^1$H NMR (Me$_2$SO-d$_6$) δ 7.94 (d, 1, H-6, J$_{5,6}$=7.5 Hz); 7.12 (bs, 1, NH); 7.04 (bs, 1, NH); 6.33 (d, 1, H-1, J$_{1',2'}$=4.6 Hz); 5.70 (d, 1, H-5); 5.61 (bd, 1, 2'-OH, J$_{2',2'-OH}$=3.1 Hz); 5.38 (bd, 1, 3'-OH, J$_{3',3'-OH}$=3.5 Hz); 5.08 (bt, 1, 5'-OH, J$_{5',5'-OH}$= 4.9 Hz); 4.00–3.93 (m, 2, H-2', H-3'); 3.78 (m, 1, H-5'$_a$); 3.61 (m, 1, H-5'$_b$); 3.16 (m, 1, H-4').

EXAMPLE 2

Preparation of 1-(4-Thio-β-D-Arabinofuranosyl)5-FluoroCytosine 1-(2,3,5-Tri-O-benzyl-4-thio-α,β--arabinofuranosyl)5-fluorocytosine (7a). To a suspension of 1-O-acetyl 2,3,5-tri-O-benzyl-4-thio-D-arabinofuranose (478 mg, 1 mmol) and cytosine (129.0 mg, 1 mmol) in anhydrosis acetonitrile (25 mmol) were added consecutively hexamethyldisilazane (HMDS, 162 mg, 1 mmol) and chlorotrimethylsilane (TMSCl, 434 mg, 4 mmol), and the mixture was stirred at room temperature for 0.5 hours. This solution was cooled to −78° C. Trimethylsilyltrifluoromethane sulfonate (267 mg, 1.2 mmol) was added and the resulting solution was stirred at −78° C. for another 2.5 h, after which time the reaction was essentially complete. The mixture was warmed to room temperature, concentrated to a small volume (5 mL), diluted with methylene chloride (50 mL) and then washed with water (20 mL) followed by saturated sodium bicarbonate and water. The organic layer was dried over MgSO$_4$ and evaporated to dryness. The residue was purified by chromatography over silica gel (50 g. elution with CHCl$_3$/MEOH 98:2) to afford 7 as 2:1α,β mixture(425.2 mg 80.0%) as a colorless syrup TLC (95:5 CHCl$_3$/MEOH) R$_f$ 0.65; MS z/e 553 (M+Li)$^+$.

$^1$H NMR (CDCl$_3$) δ 8.40 (d, 1, H-6$_β$, J=7.6);8.10 (d, 1, H-6$_α$, J$_{5,6}$=7.5 Hz); 7.38–7.09 (m, 30, aromatic H's); 6.55 (d, 1, H-1'$_β$, J$_{1',2'}$=5.7 Hz); 6.25 (d, 1, H-1'$_α$, J$_{1',2'}$=1.2 Hz); 4.90 (d, 1, H-5$_α$); 4.78 (d, 1, H-5$_β$); 4.30-4.55 (overlapping multiplets, 12, C$_6$H$_5$CH$_2$), 4.15 (dd, 1 H-2'$_β$, J$_{2',3'}$=6.8 Hz);

4.10 (m, 1, H-3'$_\alpha$, J$_{3',4'}$=1 Hz); 3.90 (dd, 1, H-3'$_\beta$, J$_{3',4'}$=6.4 Hz); 3.75 (m, 1, H-2'$_\alpha$, J$_{2',3'}$=1.7 Hz); 3.70 (m, 1, H-4'$_\alpha$); 3.65 (m, 1, H-5'$_\alpha$); 3.50–3.55 (m, 2, H-5'$_\beta$); 3.45 (m, 1, H-5'$_\alpha$); 3.40 (m, 1, H-4'$_\beta$).

1-(4-Thio-β-D-arabinofuranosyl)5-fluorocytosine (10a). To a solution of boron trichloride (1 M solution) in dry dichloromethane (7 mL, 7 mmol) cooled to −78° C., was added dropwise over a period of 30 min, a solution of compound 7 (2273 mg, 0.5 mmol) in dry dichloromethane (10 mL). Stirring was continued overnight at −20° C. The solvent was removed in vacuo and the residue was coevaporated with dichloromethane (4×20 mL). The residue was neutralized with saturated NaHCO$_3$ (25 mL) and washed with chloroform (15 mL). The aqueous layer was applied to a cation exchange (H$^+$) column and eluted with water to remove salts and then eluted with 1N NH$_4$OH to obtain the desired compound 8a as 2:1 α,β mixture which upon crystallization with water gave pure 10a (32.2 mg, 25%) MS z/e 278(M+H)$^+$.

$^1$H NMR (Me$_2$SO-d$_6$) δ 8.15 (d, 1, H-6, J$_{5,6}$=7.5 Hz); 7.75 (bs, 1, NH); 7.50 (bs, 1, NH); 6.25 (d, 1, H-1', J$_{1',2'}$=4.6 Hz); 5.65 (d, 1, H-5); 5.60 (bd, 1, 2'-OH, J$_{2',2'-OH}$=3.1 Hz); 5.40 (bd, 1, 3'-OH, J$_{3',3'-OH}$=3.5 Hz); 5.20 (bt, 1, 5'-OH, J$_{5',5'-OH}$=4.9 Hz); 4.00–3.90 (m, 2, H-2', H-3'); 3.75 (m, 1, H-5'$_a$); 3.65 (m, 1, H-5'$_b$); 3.15 (m, 1, H-4').

EXAMPLE 3

The following in vitro tests were carried out.

TABLE 1

| | IC$_{50}$ Molar Values | | |
|---|---|---|---|
| | ThioaraC | 5-fluorothioaraC | Cytosine arabinoside |
| LOX IMV1 Melanoma | 7 × 10$^{-6}$ | 6 × 10$^{-6}$ | 1 × 10$^{-6}$ |
| PC-3 Prostate | 8 × 10$^{-6}$ | 1 × 10$^{-4}$ | 5 × 10$^{-6}$ |
| ZR-75-1 Mammary | 3 × 10$^{-6}$ | 6 × 10$^{-7}$ | 4 × 10$^{-7}$ |
| CAK1-1 Renal | 3 × 10$^{-6}$ | 2 × 10$^{-5}$ | 6 × 10$^{-7}$ |
| DLD-1 Colon | 7 × 10$^{-6}$ | 8 × 10$^{-5}$ | 5 × 10$^{-6}$ |
| NC1-H23 Lung | 5 × 10$^{-6}$ | 3 × 10$^{-6}$ | 3 × 10$^{-7}$ |
| SK-MEL 28 Melanoma | 7 × 10$^{-6}$ | — | 2 × 10$^{-6}$ |
| SNB-7 (CNS) | 1 × 10$^{-6}$ | 4 × 10$^{-6}$ | 2 × 10$^{-7}$ |

The above tests were carried out with a 72 hour exposure to the compound using Natural Red assay for all cell lines except SK-MEL 28 which was done with SRB assay.

EXAMPLE 4

The following in vivo tests were carried out to illustrate the effectiveness of the compounds of the present invention.

TABLE 2

Response of SC Colon 36 Tumor to Treatment

| Treatment | | | | | Tumor Regression | | | | | |
|---|---|---|---|---|---|---|---|---|---|---|
| Agent | Dose Mg/Kg | Rt | Schedule | Non-Specific Deaths/ Total | Number of Partial | Number of Complete | Duration Med/Range (Days) | Tumor Free Surv/Total | Days to 2 Doubling | Days Delay (T − C) |
| Control | | IP | Q 4HX 3 Day 9–17 | | | | | 0/10 | 10.5 | |
| 1-(4-thio-β-D-arabinofuransyl)cytosine (prepare in saline/injection volume .5 cc/20 g. body weight | 8 | IP | Q 4HX 3 day 9–17 | 0/5 | 0 | 4 | | 4/5 | >49.0 | >38.5 |
| Palmo-ARA-C (prepared in saline/injection volume .5 cc/20 g body weight | 18 | IP | Q 1DX 9 day 9 | 0/5 | 0 | 5 | 34.6 35–35 | 4/5 | >49.0 | >38.5 |

Palmo-ARA-C is a prodrug of ARA-C.

TABLE 3

Response of SC CAKI-1 Renal Tumor to Treatment

| Treatment | | | | | Tumor Regression | | | | | |
|---|---|---|---|---|---|---|---|---|---|---|
| Agent | Dose Mg/Kg | Rt | Schedule | Non-Specific Deaths/ Total | Number of Partial | Number of Complete | Duration Med/Range (Days) | Tumor Free Surv/Total | Days to 3 Doubling | Days Delay (T − C) |
| Control | | IP | Q 4HX 3 day 7–15 | | | | | 0/12 | 9.5 | |
| 1-(4-thio-β-D-arabinofuranosyl)cytosine | 16 | IP | Q 4HX 3 day 7–15 | 1/6 | 0 | 5 | 26.9 16–48 | 0/6 | 59.8 | 50.3 |
| 1-(4-thio-β-D-arabinofuranosyl)cytosine prepared in saline; injection volume: 0.5 cc/20 g body weight | 8 | IP | Q 4HX 3 day 7-15 | 0/6 | 1 | 4 | 12.7 9–18 | 0/6 | 50.7 | 41.2 |

TABLE 3-continued

Response of SC CAKI-1 Renal Tumor to Treatment

| Treatment | | | | Tumor Regression | | | | | Days Delay |
|---|---|---|---|---|---|---|---|---|---|
| Agent | Dose Mg/Kg | Rt | Schedule | Non-Specific Deaths/Total | Number of Partial | Number of Complete | Duration Med/Range (Days) | Tumor Free Surv/Total | Days to 3 Doubling | (T − C) |
| ARA-C | 30 | IP | Q 4HX 3 day 7–15 | 5/6 | 0 | 0 | | 0/6 | 25.7 | 16.2 (Toxic) |
| ARA-C | 20 | IP | Q 4HX 3 day 7–15 | 5/6 | 0 | 0 | | 0/6 | 15.7 | 6.2 (Toxic) |
| ARA-C prepared in saline; injection volume: 0.1 cc/10 g body weight | 13.3 | IP | Q 4HX 3 day 7–15 | 0/6 | 0 | 0 | | 0/6 | 20.5 | 11.0 |
| Palmo-ARA-C | 45 | IP | Q 1DX 5 day 7 | 4/6 | 0 | 0 | | 0/6 | 41.2 | 31.7 (Toxic) |
| Palmo ARA-C prepared in saline/tween 80; injection volume 0.5 cc/20 g body weight | 22.5 | IP | Q 1DX 9 day 7 | 1/6 | 0 | 1 | 9.1 9–9 | 0/6 | 36.0 | 26.5 |

TABLE 4

Response of SC HCT-116 Colon Tumor to Treatment

| Treatment | | | | Tumor Regression | | | | | Days Delay |
|---|---|---|---|---|---|---|---|---|---|
| Agent | Dose Mg/Kg | Rt | Schedule | Non-Specific Deaths/Total | Number of Partial | Number of Complete | Duration Med/Range (Days) | Tumor Free Surv/Total | Days to 2 Doubling | (T − C) |
| Control | | IP | Q 4HX 3 day 6–14 | | | | | 0/12 | 8.9 | |
| 1-(4-thio-β-O-arabinofuransyl)cytosine | 20 | IP | Q 4HX 3 day 6–14 | 0/6 | 0 | 6 | | 6/6 | >52.0 | >43.1 |
| 1-(4-thio-β-O-arabinofuransyl)cytosine prepared in saline (soluble); injection volume 0.5 cc/20 g body weight | 13.3 | IP | Q 4HX 3 day 6–14 | 0/6 | 0 | 6 | 23.6 24–24 | 5/6 | >52.0 | >43.1 |
| ARA-C | 13.3 | IP | Q 4HX 3 day 6–14 | 0/6 | 0 | 0 | | 0/6 | 12.2 | 3.3 |
| ARA-C prepared in saline; injection volume: 0.5 cc/20 g body weight | 9 | IP | Q 4HX 3 day 6–14 | 0/6 | 0 | 0 | | 0/6 | 10.9 | 2.0 |
| Palmo-ARA-C | 22.5 | IP | Q 1DX 9 day 6 | 0/6 | 0 | 1 | 24.2 24–24 | 0/6 | 24.0 | 15.1 |
| Palmo-ARA-C prepared in saline + tween 80; injection volume: 0.5 cc/20 g body weight | 15 | IP | Q 1DX 9 day 6 | 0/6 | 0 | 0 | | 0/6 | 14.9 | 6.0 |

*Palmo-ARA-C is a prodrug of ARA-C.

As can be appreciated from the above tests, in most cell lines, ARA-C exhibits higher cytoxicity as compared to that of the present invention which would tend to discourage use of the compounds of the present invention as a cancer treatment. However, surprisingly, the 1-(4-thio-β-D-arabinofuranosyl)cytosine is more potent than ARA-C and more selective in killing cancel cells in vivo. Compounds employed according to the present invention exhibit better anticancer activity along with lower toxicity. This may be due to the fact that 1-(4-thio-β-D-arabinofuranosyl)cytosine does not get deaminated by cytidine deaminase as quickly as AraC does, which is shown below in Table 5 by using radio labeled substances. Good substrate activity of cytidine deaminase with AraC has been a major problem with this drug because it not only decreases half-life of drug but also gets converted to AraUridine which is not an active substance.

TABLE 5

Cytidine deaminase activity determined with radioactive substrates

| Compound | $K_m$ | $V_{max}$ | $V_{max}/K_{min}$ |
|---|---|---|---|
| AraC | 147 | 9 | 0.06 |
| 1-(4-thio-β-D-arabinofuranosyl cytosine | 2571 | 17 | 0.007 |

The following tests were carried out which illustrate the ability of the thioarabinofuranosyl compounds according to the present invention to inhibit DNA replication in mammalian cells. In the following tests, dCyd refers to 2'-deoxycytidine, TCyd refers to thiodeoxycytidine, T-araC refers to 1-(4-thio(3-D-arabinofuranosyl) cytasine and Ara-C refers to "cytosine arabinoside". The terms "d CTP", "T-d CTP", "ara CTP" and "T ara CTP" refer to the corresponding triphosphates. The term "dURD" refers to 2-deoxyuridine. The term "F-dUrd" refers to fluorinated deoxyuridine and "F-dUMP" refers to fluorinated deoxyuridine monophosphate.

Figure 1A:
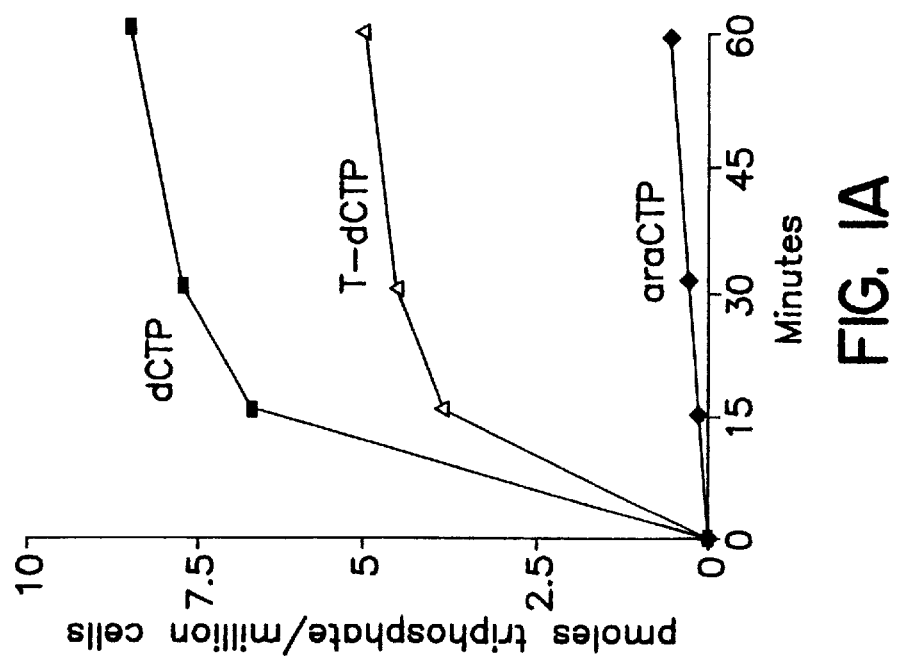

Reference is made to FIGS. 1a and 1b which illustrate the metabolism of d Cyd, T-d Cyd, ara C and T-ara C to their respective triphosphates. In particular, CEM cells were incubated with 2000 nM of [5-$^3$H]T-dCyd, 5 nM [5-$^3$H]araC, or 25 nm [5-$^3$H]T-araC for the times indicated. The radioactivity in the 5'-triphosphate peak was determined using SAX HPLC. For each compound, the amount of radioactivity in the 5'-triphosphate peak was more than 90% of the total radioactivity eluting from the SAX HPLC column.

Test results related to the inhibition of CEM cell growth are shown below in Table 6.

CEM cells were incubated with various concentrations of each compound and the effect on cell numbers was determined using a Coulter Counter. The IC$_{50}$ was determined from a plot of the percent of control growth versus drug concentration. The data presented are the mean and standard deviation from 3 separate experiments. The araC-resistant cells were obtained by incubating CEM cells in the presence of 150 nM araC for approximately 1 month at which time the CEM cells were growing at control rates.

TABLE 6

Inhibition of CEM Cell Growth by dCyd Analogs

| Compound | Wild-type IC$_{50}$ (nM) | araC-resistant IC$_{50}$ (nM) | Resistant/WT |
|---|---|---|---|
| T-dCyd | 2200 ± 1400 | 7200 ± 7600 | 3 |
| T-araC | 24 ± 9 | 125 ± 84 | 5 |
| araC | 6 ± 3 | 800 ± 400 | 145 |

Test results related to metabolism in wild-type and araC resistant CEM cells are shown below in Table 7.

CEM cells (wild-type or araC-resistant cells) were incubated with 100 nM of [5-$^3$H]dCyd, [5-$^3$H]T-dCyd, [5-$^3$H]araC, or [5-$^3$H]T-araC for the times indicated. The radioactivity in the 5'-triphosphate peak and the incorporation of radioactivity in the acid-insoluble fraction (DNA) was determined. For each compound, the amount of radioactivity in the 5'-triphosphate peak was more than 90% of the total radioactivity eluting from the SAX HPLC column.

TABLE 7

Metabolism of dCyd and Its Analogs in Wild-Type and araC Resistant CEM Cells

| Compound | Incubation time Hours | Cell type | Triphosphate | DNA | Total |
|---|---|---|---|---|---|
| | | | pmoles/10$^6$ cells (percent of WT) | | |
| dCyd | 0.25 | WT | 2.27 | 1.19 | 3.46 |
| | | Resistant | 0.021 (0.93) | 0.011 (0.89) | 0.032 (0.91) |
| T-dCyd | 0.25 | WT | 0.877 | 1.29 | 2.17 |
| | | Resistant | 0.036 (4.1) | 0.051 (4.0) | 0.087 (4.0) |
| araC | 1 | WT | 14.7 | 0.28 | 14.98 |
| | | Resistant | 0.19 (1.2) | 0.018 (6.3) | 0.208 (1.4) |
| T-araC | 1 | WT | 0.202 | 0.0056 | 0.2076 |
| | | Resistant | 0.051 (25) | 0.0025 (45) | 0.0535 (26) |

Results illustrating photphorylation in cell-free CEM extracts are shown below in Table 8.

A crude cell extract was prepared from wild-type and araC-resistant CEM cells and the ability to phosphorylate dCyd, araC, and T-araC was determined. The number in parentheses is the number of experiments performed. Reactions were performed in solutions containing 50 mM Tris (pH 8.0), 5 mM ATP, 7.5 mM MgCl$_2$, 20 mM NaF, extract, and 1 $\mu$m [5-$^3$H]dCyd, [5-$^3$H]araC or [5-$^3$H]T-araC. At various times after the initiation of the experiment, an aliquot of each reaction volume was removed and placed on DE-81 filters. The filters were washed with 1 mM ammonium formate and ethanol, and the amount of radioactivity on each filter was determined. The phosphorylation of each compound increased in a linear manner with respect to time. This assay was verified by HPLC.

TABLE 8

Phosphorylation of dCyd, araC, and T-araC in Cell-Free CEM Extracts

| Compound | Wild-type | araC-resistant CEM cells | Percent of wild-type |
|---|---|---|---|
| | pmoles/mg protein/minute | | |
| dCyd | 240 ± 33 (3) | 3.5 ± 0.2 (3) | 1.5 |
| araC | 94 (1) | 1.2 (1) | 1.3 |
| T-araC | 0.83 (2) | 0.011 (1) | 1.3 |

Table 9 below illustrates deoxycydidine deaminase activity. In particular, deoxycytidine deaminase activity was purified from Molt-4 cells as described (Shewach et al, *Mol. Pharmacol.* 42: 518–524, 1992). Each assay was done in duplicate and the kinetic constants were determined from linear double-reciprocal plots of 1/velocity versus 1/concentration of the substrate. The best line was determined by linear regression from at least 5 datum points, and the K$_m$ and V$_{max}$ were determined from the x and y intercepts.

TABLE 9

Substrate Characteristics of dCyd, araC, and T-araC with dCyd Kinase Activity Isolated from Molt-4 Cells

| Compound | K$_m$ ($\mu$M) | Relative V$_{max}$ | V$_{max}$/K$_m$ |
|---|---|---|---|
| dCyd | 1.2 | 1 | 0.8 |
| araC | 15 | 0.1 | 0.006 |
| 4'-thio-araC | 93 | 0.46 | 0.005 |

Table 10 below also illustrates deoxycytidine deaminase activity.

Deoxycytidine deaminase activity was purified from human placenta and the K$_m$ and V$_{max}$ of dCyd, T-dCyd, araC, and T-araC were determined. Reactions were carried out in solutions containing 20 mM potassium phosphate (pH 7.4), 100 mM KCl, various concentrations of radiolabeled nucleoside, and enzyme. The reactions were stopped with acid, the substrate was separated from the product by paper chromatography, and the radioactivity in each were determined. The kinetic constants were determined from linear double-reciprocal plots of 1/velocity versus 1/concentration of the substrate. The best line was determined by linear regression from at least 5 datum points, and the K$_m$ and V$_{max}$ were determined from the x and y intercepts. The data presented are the mean and standard deviation from 3 separate experiments.

TABLE 10

Substrate Characteristics of dCyd, T-dCyd, araC, and T-araC
with dCyd Deaminase Activity Isolated from Human Placenta

| Compound | $K_m$ ($\mu$M) | $V_{max}$ (pmoles/mg/ml) | $V_{max}/K_m$ |
|---|---|---|---|
| dCyd | 23 ± 2.7 | 13 ± 1.5 | 0.55 |
| T-dCyd | 111 ± 77 | 37 ± 12 | 0.33 |
| araC | 238 ± 131 | 14 ± 7 | 0.058 |
| T-araC | 2944 ± 1023 | 21 ± 6 | 0.0072 |

Results of half-life tests in CEM cells are reported below in Table 11.

After incubation of CEM cells for 1 hour with 100 nM of [5-$^3$H]dCyd, [5-$^3$H]T-dCyd, [5-$^3$H]araC, or [5-$^3$H]T-araC, the cells were collected, washed with fresh medium, and resuspended in fresh medium that did not contain radiolabeled nucleosides. Samples were collected at various times after the cells were resuspended in fresh medium, and the amount of radioactivity in the 5'-triphosphate peak was determined using SAX HPLC. The data presented are the mean and standard deviation from 3 separate experiments.

TABLE 11

Initial Half-Life of dCTP, T-dCTP, araCTP,
and T-araCTP in CEM Cells

| Nucleotide | Hours (SD) |
|---|---|
| dCTP | 0.94 ± 0.16 |
| T-dCTP | 1.10 ± 0.35 |
| araCTP | 5.31 ± 0.31 |
| T-araCTP | 10.8 ± 1.80 |

Figure 2:
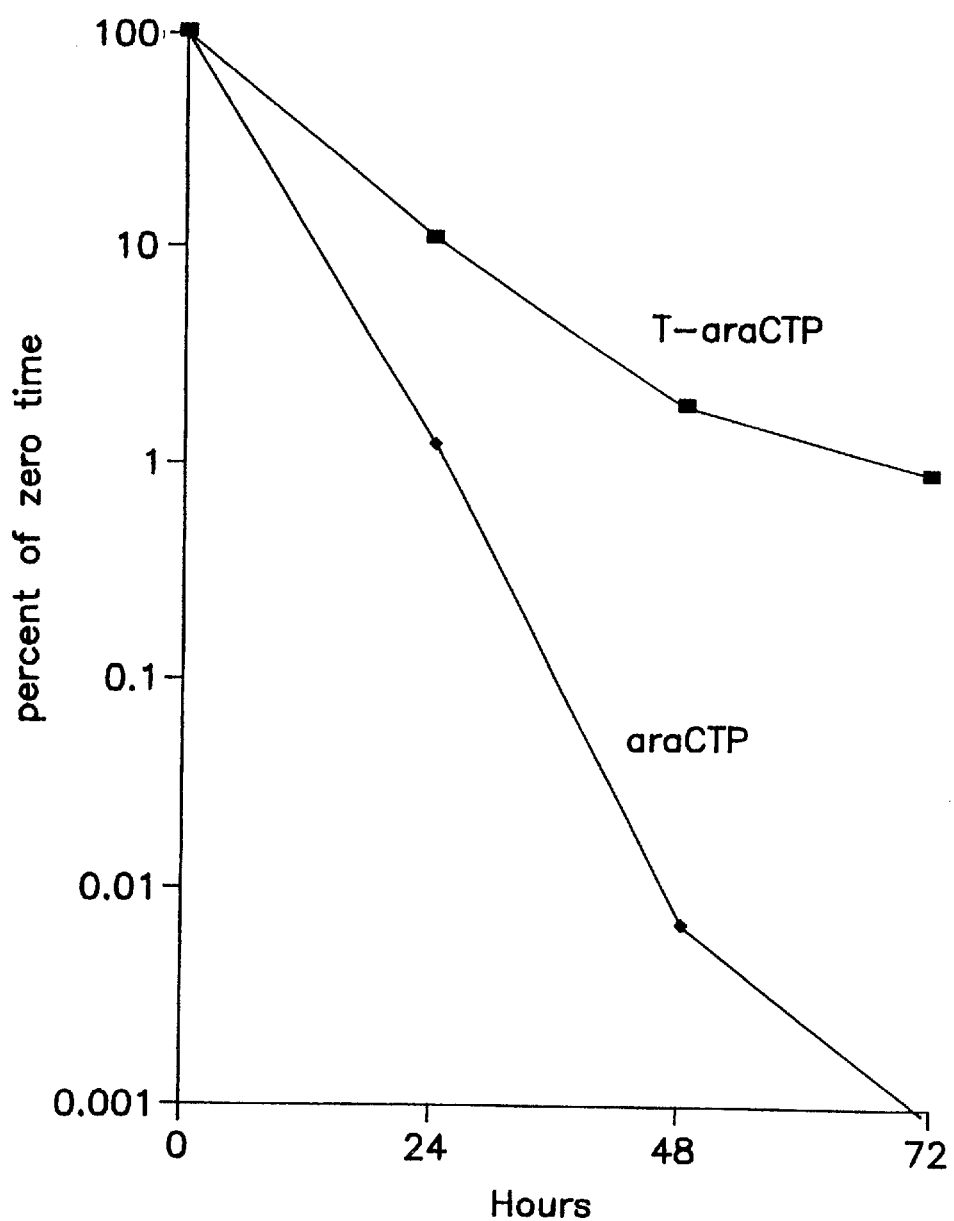
FIG. 2 is a graph showing the retention of ara c triphosphate and thio ara c triphosphate in CEM cells.

Results of tests related to retention of araCTP and T-araCTP in CEM cells are shown in FIG. 2. The tests were carried out as follows:

After incubation of CEM cells for 1 hour with either 5 nM [5-$^3$H]araC or 200 nm [5-$^3$H]T-araC, the cells were collected, washed with fresh medium, and resuspended in fresh medium that did not contain radiolabeled nucleosides. Samples were collected at various times after the cells were resuspended in fresh medium, and the amount of radioactivity in the 5'-triphosphate peak was determined using SAX HPLC. In this experiment there was 0.639 pmoles araCTP/$10^6$ cells and 0.246 pmoles of T-araCTP after the 1 hour incubation with radiolabeled compound.

Results related to metabolism in CEM cells are reported below in Table 12. In particular, CEM cells were incubated with 100 nM of [5-$^3$H]dCyd, [5-$^3$H]T-dCyd, [5-$^3$H]araC, or [5-$^3$H]T-araC for the times indicated. The complete metabolism of each compound was determined: The medium was analyzed for the original compound, its deaminated form using reverse phase HPLC, and H$_2$O; the acid-soluble extract was analyzed by SAX HPLC for phosphorylated metabolites; and the incorporation of radioactivity into acid-precipitable material (DNA) was determined. All of the original radioactivity was accounted for in these fractions. For each compound, the amount of radioactivity in the 5'-triphosphate peak was more than 90% of the total radioactivity eluting from the SAX HPLC column.

TABLE 12

Metabolism of dCyd, T-dCyd, araC, and T-araC in CEM Cells

| Nucleoside | Time of Incubation (hours) | Original Compound | Deaminated Compound | H$_2$O | nucleoside-TP | DNA |
|---|---|---|---|---|---|---|
| | | | (percent of total) | | | |
| dCyd | 1 | 38 | 0 | 55 | 4 | 3 |
| T-dCyd | 1 | 90 | 0 | 0 | 2 | 8 |
| araC | 1 | 87 | 0 | 0 | 13 | 0.4 |
| T-araC | 24 | 96 | 0 | 0 | 4 | 0.3 |

Results from tests related to the effect of F-dUrd on metabolism are shown below in Table 13.

CEM cells were incubated with 100 nM of [5-$^3$H]dCyd, [5-$^3$H]T-dCyd, [5-$^3$H]araC, or [5-$^3$H]T-araC for the times indicated in the presence or absence of 10 $\mu$m F-dUrd, which is metabolized to F-dUMP (a potent inhibitor of thymidylate synthetase). The complete metabolism of each compound was determined as described in the legend to Table 12, and the percent of deaminated metabolites for each compound was determined. In the absence of F-dUrd, the deaminated product for dCyd was [$^3$H]H$_2$O due to the removal of [$^3$H] at the 5 position of F-dUMP by thymidylate synthetase. In the presence of F-dUrd, the deaminated product of dCyd, T-dCyd, and araC was in the medium as dUrd, T-dUrd, or araU, respectively.

TABLE 13

Effect of F-dUrd on the Metabolism of
dCyd, T-dCyd, araC, or T-araC

| Compound | F-dUrd ($\mu$M) | Incubation time (hours) | Percent Deamination |
|---|---|---|---|
| dCyd | 0 | 1 | 32 |
| dCyd | 10 | 1 | 22 |
| T-dCyd | 0 | 8 | 0 |
| T-dCyd | 10 | 8 | 24 |
| araC | 0 | 8 | 0 |
| araC | 10 | 8 | 10 |
| T-araC | 0 | 24 | 0 |
| T-araC | 10 | 24 | 0 |

Table 14 below reports results of tests concerning effects of DNA, RNA and protein synthesis.

CEM cells were incubated with 60 $\mu$M T-dCyd, 150 nM araC, or 750 nM T-araC. Radiolabeled precursors of DNA ([$^3$H]dThd, RNA ([$^3$H]Urd), or protein ([$^3$H]leucine) were added to each treatment 30 minutes after the addition of each compound. Samples were taken 1, 2, 3 and 4 hours after the addition of radiolabeled precursors, and the incorporation of radioactivity into RNA, DNA, or protein were determined as described (Parker et al, *Biochem. Pharmacol.* 55: 1673–1681, 1998). Each number represents the average of two experiments.

TABLE 14

Effect of T-dCyd, araC, and T-araC on
DNA, RNA, and Protein Syntheses

| Compound | DNA | RNA | protein |
|---|---|---|---|
| | Percent of control | | |
| 60 $\mu$M T-dCyd | 38 | 95 | 78 |
| 150 nM araC | 8 | 96 | 96 |
| 750 nM T-araC | 16 | 87 | 72 |

As can be appreciated from the above, thioarobinofuranosyl compounds according to the present invention can be used to inhibit DNA replication in mammalian cells. These results tend to suggest their ability as immunomodulators, which would render them suitable for treating autoimmune diseases. This is further supported by the fact that several guanosine analogs have been shown to stimulate the immune system (Weigle, W. O., *CRD Crit.Rev.Immunol.*, 1987, 7, 285; Lin et al, *J.Med. Chem.*, 1985, 28, 1194–1198; Reitz et al, *J.Med. Chem.*, 1994, 37, 3561–3578; Michael et al., *J.Med. Chem.*, 1993, 36, 3431–3436). Certain 3-β-ribofuranosylthiazolo[4,5-d]pyrimidines have also been shown to have significant immunoactivity, including murine spleen cell proliferation and in vivo activity against Semliki Forest virus (Nagahara et al., *J.Med. Chem.*, 1990, 33, 407–415).

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A method for treating a solid tumor in a mammalian host in need of such treatment wherein the solid tumor is sensitive to at least one compound represented by the formula 1, which comprises administering to said host an effective anti-solid tumor amount of at least one compound represented by the formula 1:

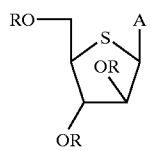

(1)

wherein each R individually is H, an aliphatic acyl group or an aromatic acyl group;

A is selected from the group consisting of

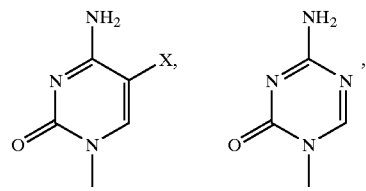

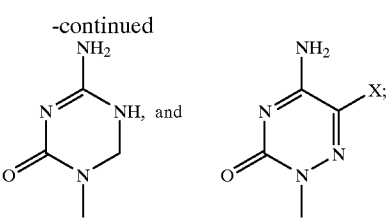

wherein X is selected from the group consisting of hydrogen, fluorine, alkoxy, alkyl, haloalkyl, alkenyl, haloalkenyl, alkynyl, amino, monoalkylamino, dialkylamino, cyano and nitro, thereby treating the solid tumor in the mammalian host.

2. The method of claim 1 wherein each R is H.

3. The method of claim 1 wherein A is

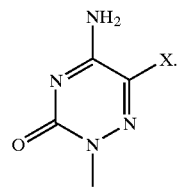

4. The method of claim 3 wherein X is H.

5. The method of claim 1 wherein X is H.

6. The method of claim 1 wherein said compound is 1-(4-thio-β-D-arabinofuranosyl) cytosine.

7. The method of claim 1 wherein A is:

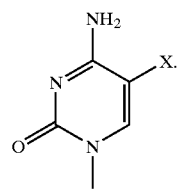

8. The method of claim 7 wherein X is H.

9. A method for treating a mammalian host suffering from a cancer selected from the group consisting of melanoma, prostate cancer, mammary cancer, renal cancer, colon cancer and lung cancer, which comprises administering to said host an effective anticancer amount of at least one compound represented by the formula 1.

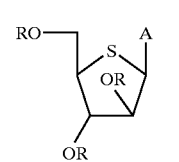

(1)

wherein each R individually is H, an aliphatic acyl group or an aromatic acyl group;

A is selected from the group consisting of

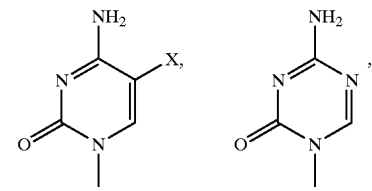

-continued

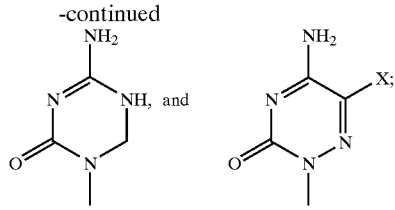

wherein X is selected from the group consisting of hydrogen, fluorine, alkoxy, alkyl, alkyl, haloalkyl, alkenyl, haloalkenyl, allynyl, amino, monoalkylamino, dialkylammo, cyano and nitro, thereby treating the mammalian host.

10. The method of claim 9 wherein each R is H.
11. The method of claim 9 wherein each A is:

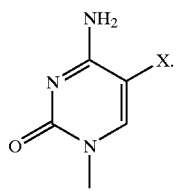

12. The method of claim 11 wherein X is H.
13. The method of claim 9 wherein X is H.
14. A method for treating a nmalian host suffering from a cancer selected from the group consisting of melanoma, prostate cancer, mammary cancer, renal cancer, colon cancer and lung cancer, which comprises administering to said host an effective anticancer amount of 1-(4-thio-β-D-arabinofuranosyl) cytosine, thereby treating the mammalian host.
15. The method of claim 14 wherein said cancer is mammary cancer or renal cancer.
16. The method of claim 14 wherein said cancer is melanoma.
17. The method of claim 14 wherein said cancer is prostate cancer.
18. The method of claim 14 wherein said cancer is mammary cancer.
19. The method of claim 14 wherein said cancer is renal cancer.
20. The method of claim 14 wherein said cancer is colon cancer.
21. The method of claim 14 wherein said cancer is lung cancer.

\* \* \* \* \*